US 8,318,695 B2
Nov. 27, 2012

(12) United States Patent
Stroumpoulis et al.

(54) TUNABLY CROSSLINKED POLYSACCHARIDE COMPOSITIONS

(75) Inventors: Dimitrios Stroumpoulis, Goleta, CA (US); Ahmet Tezel, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 12/178,574

(22) Filed: Jul. 23, 2008

(65) Prior Publication Data

US 2009/0036403 A1     Feb. 5, 2009

Related U.S. Application Data

(60) Provisional application No. 60/952,770, filed on Jul. 30, 2007.

(51) Int. Cl.
*A61K 31/715* (2006.01)

(52) U.S. Cl. .......................................................... 514/54

(58) Field of Classification Search .................. None
See application file for complete search history.

(56) References Cited

U.S. PATENT DOCUMENTS

| | | | |
|---|---|---|---|
| 2,128,827 A | 8/1938 | Killian |
| 3,763,009 A | 10/1973 | Suzuki |
| 4,582,865 A | 4/1986 | Balazs et al. |
| 4,605,691 A | 8/1986 | Balazs et al. |
| 4,636,524 A | 1/1987 | Balazs |
| 4,713,448 A | 12/1987 | Balazs |
| 4,716,154 A | 12/1987 | Malson et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,356,883 A | 10/1994 | Kuo et al. |
| 5,399,351 A | 3/1995 | Leshchiner et al. |
| 5,531,716 A | 7/1996 | Luzio et al. |
| 5,571,503 A | 11/1996 | Mausner |
| 5,616,568 A | 4/1997 | Pouyani et al. |
| 5,616,611 A | 4/1997 | Yamamoto |
| 5,633,001 A | 5/1997 | Agerup |
| 5,643,464 A | 7/1997 | Rhee et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,767,924 B2 | 7/2004 | Yu et al. |
| 6,767,928 B1 | 7/2004 | Murphy et al. |
| 6,893,466 B2 | 5/2005 | Trieu |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,192,984 B2 | 3/2007 | Berg |

(Continued)

FOREIGN PATENT DOCUMENTS

CA            949965        6/1974

(Continued)

OTHER PUBLICATIONS

Leach, J. B. et al., Journal of Biomedical Materials Research Part A, "Development of photocrosslinkable hyaluronic acid-polyethylene glycol-peptide composite hydrogels for soft tissue engineering", vol. 70A, issue 1, pp. 74-82, Jul. 2004.*

(Continued)

*Primary Examiner* — Layla Bland
*Assistant Examiner* — Bahar Schmidtmann
(74) *Attorney, Agent, or Firm* — Linda Fox; Stephen Donovan; Debra Condino

(57) ABSTRACT

The present invention generally relates to novel biocompatible crosslinked polysaccharide gel compositions, methods of their manufacture and use, and the novel crosslinkers used to make them. In one aspect of the invention, a novel polyethylene glycol crosslinking agent is described for crosslinking hyaluronic acid. In another aspect of the invention, novel crosslinking agents comprising more than two functional groups are described. These multifunctional crosslinking agents can be used on their own to crosslink hyaluronic acid, or they may be combined with bifunctional crosslinking agents in varying ratios to make hyaluronic acid of tunable mechanical strength and hardness. The present invention also discloses novel hyaluronic acid compositions that have been coated with polyethylene glycol and methods of their use.

18 Claims, 2 Drawing Sheets

U.S. PATENT DOCUMENTS

| | | | |
|---|---|---|---|
| 7,314,636 | B2 | 1/2008 | Caseres et al. |
| 7,741,476 | B2 | 6/2010 | Lebreton |
| 7,902,171 | B2 | 3/2011 | Reinmuller et al. |
| 2002/0102311 | A1 | 8/2002 | Gustavsson et al. |
| 2002/0160109 | A1 | 10/2002 | Yeo et al. |
| 2003/0031638 | A1 | 2/2003 | Joshi et al. |
| 2003/0093157 | A1 | 5/2003 | Casares et al. |
| 2003/0148995 | A1 | 8/2003 | Piron et al. |
| 2004/0032056 | A1 | 2/2004 | Vang et al. |
| 2004/0101959 | A1 | 5/2004 | Marko et al. |
| 2004/0127698 | A1 | 7/2004 | Tsai et al. |
| 2004/0127699 | A1 | 7/2004 | Zhao et al. |
| 2004/0199241 | A1 | 10/2004 | Gravett et al. |
| 2004/0265389 | A1 | 12/2004 | Yui et al. |
| 2005/0101582 | A1 | 5/2005 | Lyons et al. |
| 2005/0136122 | A1 | 6/2005 | Sadozai et al. |
| 2005/0142152 | A1 | 6/2005 | Leshchiner et al. |
| 2005/0181007 | A1 | 8/2005 | Hunter |
| 2005/0186261 | A1 | 8/2005 | Avelar |
| 2005/0226936 | A1 | 10/2005 | Agerup |
| 2005/0271729 | A1 | 12/2005 | Wang |
| 2005/0287180 | A1 | 12/2005 | Chen |
| 2006/0040894 | A1 | 2/2006 | Hunter et al. |
| 2006/0095137 | A1 | 5/2006 | Chung et al. |
| 2006/0122147 | A1 | 6/2006 | Wohlrab |
| 2006/0141049 | A1 | 6/2006 | Lyons et al. |
| 2006/0194758 | A1 | 8/2006 | Lebreton |
| 2006/0246137 | A1 | 11/2006 | Hermitte et al. |
| 2006/0257488 | A1 | 11/2006 | Hubbard |
| 2006/0286769 | A1 | 12/2006 | Tsuchiya et al. |
| 2007/0026070 | A1 | 2/2007 | Vonwiller et al. |
| 2007/0066816 | A1 | 3/2007 | Tsai et al. |
| 2007/0077292 | A1 | 4/2007 | Pinsky |
| 2007/0203095 | A1 | 8/2007 | Sadozai et al. |
| 2007/0212385 | A1 | 9/2007 | David |
| 2007/0224247 | A1 | 9/2007 | Chudzik |
| 2007/0224278 | A1 | 9/2007 | Lyons et al. |
| 2007/0298005 | A1 | 12/2007 | Thibault |
| 2008/0044476 | A1 | 2/2008 | Lyons et al. |
| 2008/0089918 | A1 | 4/2008 | Lebreton |
| 2008/0188416 | A1 | 8/2008 | Bernstein |
| 2008/0193538 | A1 | 8/2008 | Kitazono et al. |
| 2008/0200430 | A1 | 8/2008 | Bitterman et al. |
| 2008/0207794 | A1 | 8/2008 | Wright et al. |
| 2008/0241252 | A1 | 10/2008 | Lyons |
| 2008/0268051 | A1 | 10/2008 | Lyons |
| 2008/0274946 | A1 | 11/2008 | Gimpapa |
| 2008/0279806 | A1 | 11/2008 | Cho |
| 2009/0018102 | A1 | 1/2009 | Moutet |
| 2009/0022808 | A1 | 1/2009 | Champion |
| 2009/0028817 | A1 | 1/2009 | Niklason et al. |
| 2009/0036403 | A1 | 2/2009 | Stroumpoulis |
| 2009/0042834 | A1 | 2/2009 | Karageozian et al. |
| 2009/0093755 | A1 | 4/2009 | Schroeder |
| 2009/0110671 | A1 | 4/2009 | Miyata et al. |
| 2009/0110736 | A1 | 4/2009 | Boutros |
| 2009/0143331 | A1 | 6/2009 | Stroumpoulis et al. |
| 2009/0143348 | A1 | 6/2009 | Tezel |
| 2009/0148527 | A1 | 6/2009 | Robinson |
| 2009/0155314 | A1 | 6/2009 | Tezel |
| 2009/0169615 | A1 | 7/2009 | Pinsky |
| 2009/0263447 | A1 | 10/2009 | Asius et al. |
| 2009/0291986 | A1 | 11/2009 | Pappas et al. |
| 2009/0297632 | A1 | 12/2009 | Waugh |
| 2010/0004198 | A1 | 1/2010 | Stroumpoulis et al. |
| 2010/0028437 | A1 | 2/2010 | Lebreton |
| 2010/0035838 | A1 | 2/2010 | Heber et al. |
| 2010/0041788 | A1 | 2/2010 | Voigts et al. |
| 2010/0098764 | A1 | 4/2010 | Stroumpoulis et al. |
| 2010/0099623 | A1 | 4/2010 | Schroeder et al. |
| 2010/0111919 | A1 | 5/2010 | Abuzaina et al. |
| 2010/0136070 | A1 | 6/2010 | Dobak et al. |
| 2010/0226988 | A1 | 9/2010 | Lebreton |

FOREIGN PATENT DOCUMENTS

| | | |
|---|---|---|
| EP | 0273823 | 7/1988 |
| EP | 0416250 | 3/1991 |
| EP | 0416846 | 3/1991 |
| EP | 1247522 | 10/2002 |
| EP | 141792 | 4/2003 |
| EP | 1419792 | 4/2003 |
| EP | 1398131 | 3/2004 |
| EP | 1726299 | 11/2006 |
| EP | 2236523 | 10/2010 |
| FR | 2733427 | 10/1996 |
| FR | 2920000 | 2/2009 |
| FR | 2924615 | 6/2009 |
| JP | 55-153711 | 11/1980 |
| JP | 2007063177 | 3/2007 |
| WO | WO 86/00079 | 1/1986 |
| WO | WO 86/00912 | 2/1986 |
| WO | WO 92/00105 | 1/1992 |
| WO | WO 92/20349 | 11/1992 |
| WO | WO 94/01468 | 1/1994 |
| WO | WO 94/02517 | 2/1994 |
| WO | WO 96/33751 | 1/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 02/05753 | 1/2002 |
| WO | WO 02/06350 | 1/2002 |
| WO | WO 02/09792 | 2/2002 |
| WO | WO 02/17713 | 3/2002 |
| WO | WO 03/007782 | 1/2003 |
| WO | WO 2004/020473 | 3/2004 |
| WO | WO 2004/022603 | 3/2004 |
| WO | WO 2004/073759 | 9/2004 |
| WO | WO 2004/092223 | 10/2004 |
| WO | WO 2005/040224 | 5/2005 |
| WO | WO 2005/067944 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2008/034176 | 3/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |

OTHER PUBLICATIONS

Bulpitt, P. et al., J Biomed Mater Res, "New Strategy for Chemical Modification of Hyaluronic Acid: Preparation of Functionalized Derivatives and Their Use in the Formation of Novel Biocompatible Hydrogels", 1999, vol. 47, pp. 152-169.*

Shu, X. Z. et al., Biomaterials, "In situ crosslinkable hyaluronan hydrogels for tissue engineering", 2004, vol. 25, pp. 1339-1348.*

Aesthetic Buyers Guide, Juvederm Raises Stardards, Jan./Feb. 2007, pp. 5. www.miinews.com.

McPherson et al., Development and Biochemical Characterization of Injectable Collagen, J. Dermatol Surg Oncol, 1988, 14, Supp 1.

*Aesthetic Buyers Guide*, "Juvéderm Raises Standards"; Jan./Feb. 2007 (5 pp.), www.miinews.com.

Adams; "An Analysis of Clinical Studies of the Uses of Crosslinked Hyaluronan, Hylan, in the Treatment of Osteoarthritis"; J. Rheumatol Suppl.; vol. 39; pp. 16-18; Aug. 1993.

Albano et al.; "Hyroxyethyl Radicals in Ethanol Hepatotoxicity"; Frontiers in Bioscience; vol. 4; pp. 533-540; 1999.

Allemann et al.; "Hyaluronic acid gel (JUVADERM) preparations in the treatment of facial wrinkles and folds"; Clinical Interventions in Aging; vol. 3, No. 4; pp. 629-634; 2008.

Antunes et al.; "Efficacy of Intrarectal Lidocaine Hydrochloride Gel for Pain control in Patients Undergoing Transrectal Prostate Biopsy"; International Braz J Urol; vol. 30, No. 5; pp. 380-383; Sep.-Oct. 2004.

Atanassoff et al.; "The Effect of Intradermal Administration of Lidocaine and Morphine on the Response to Thermal Stimulation"; Anesth Analg; vol. 84; pp. 1340-1343; 1997.

Baumann et al.; "Comparison of smooth-gel hyaluronic acid dermal fillers with cross-linked bovine collagen: a multicenter, double-masked, randomized, within-subject study"; Dermatol. Surg.; vol. 33(Suppl 2); pp. S128-S135 2007.

Beasley et al.; "Hyaluronic acid fillers: a comprehensive review"; Facial Plast. Surg.; vol. 25, No. 2; pp. 86-94; 2009.

Beer; "Dermal fillers and combinations of fillers for facial rejuvenation"; Dermatol. Clin.; vol. 27, No. 4; pp. 427-432; 2009.

Belda et al.; "Hyaluronic acid combined with mannitol to improve protection against free-radical endothelial damage: Experimental Model"; J.Cataract Refract Surg; Vo. 31; pp. 1213-1218; 2005.

Bircher, et al.; "Delayed-Type Hypersensitivity to Subcutaneous Lidocaine With Tolerance to Articaine: Confirmation by in Vivo and in Vitro Tests"; Contact Dermatitis; vol. 34; pp. 387-389; 1996.

Capozzi et al., "Distant Migration of Silicone Gel From a Ruptured Breast Implant", Plastic and Reconstructive Surgery; vol. 62; pp. 302-303; 1978.

Carlin et al., "Effect of anti-inflammatory drugs on xanthine oxidase and xanthine oxidase induced depolymerization of hyaluronic acid"; Agents and Actions; vol. 16 (5); pp. 377-384; 1985.

Carruthers et al.; "The science and art of dermal fillers for soft-tissue augmentation"; J. Drugs Dermatol; vol. 8(4); pp. 335-350; 2009.

Champion et al., "Role of Target Geometry in Phagocytosis"; S. Proc. Nat. Acad. Sci.; vol. 103; No. 13; pp. 4930-4934; Mar. 28, 2006.

Chin et al., "Allergic Hypersensitivity to Lidocaine Hydrochloride", International journal of Dermatology, vol. 19; pp. 147-148; Apr. 1980.

Clark et al., "The Influence of Triamcinolone Acetonide on Joint Stiffness in the Rat", J Bone Joint Surg; vol. 53-A; pp. 1409-1414; Oct. 1971.

Cohen et al., "Organization and Adhesive Properties of the Hyaluronan Pericellular Coat of Chondrocytes and Epithelial Cells", Biophys J.; vol. 85; pp. 1996-2005; Sep. 2003.

Deland, "Intrathecal Toxicity Studies with Benzyl Alcohol", Toxicol Appl Pharmacol; vol. 25; pp. 153-156; 1973.

Desai et al., J Pharm Sci Abstract only; 84 (2): 212-215; Feb. 1995.

Falcone et al.; "Crosslinked hyaluronic acid dermal fillers: a comparison of rheological properties." J Biomed Mater Res; vol. 87(1); pp. 264-271; 2008.

Falcone et al.; "Temporary polysaccharide dermal fillers: a model for persistence based on physical properties." Dermatol Surg.; vol. 35(8); pp. 1238-1243; 2009.

Farley et al., "Diluting Lidocaine and Mepivacaine in Balanced Salt Solution Reduces the Pain of Intradermal Injection", Regional Anesthesia; vol. 19(1); pp. 48-51; 1994.

Frati et al., "Degradation of hyaluronic acid by photosensitized riboflavin in vitro. Modulation of the effect by transition metals, radical quenchers, and metal chelators"; Free Radical Biology Medicine; vol. 22 (7); pp. 1139-1144 1997.

Fujinaga et al., "Reproductive and Teratogenic Effects of Lidocaine in Sprague-Dawley Rats"; Anesthesiology vol. 65; pp. 626-632; 1986.

Gammaitoni et al., "Pharmacokinetics and safety of continuously applied lidocaine patches 5%"; Am J Health Syst Pharm; vol. 59; pp. 2215-2220; Nov. 15, 2002.

GinShiCel MH Hydroxy Propyl methyl Cellulose, Web Page http://www.ginshicel.cn/MHPC.html, Nov. 12, 2008.

Gold; "Use of Hyaluronic acid fillers for the treatment of the aging face"; Clin. Interventions Aging; vol. 2(3); pp. 369-376; 2007.

Goldberg; "Breakthroughs in US dermal fillers for facial soft-tissue augmentation"; J Cosmet Laser Ther; vol. 11; pp. 240-247; 2009.

Graefe et al., "Sensitive and specific photometric determination of mannitol in human serum"; Clin Chem Lab Med; vol. 41, No. 8; pp. 1049-1055; 2003.

Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.

Hassan et al., "Effects of Adjuvants to local anaesthetics on their duration. III. Experimental studies of hyaluronic acid"; Abstract Pub Med [Acta Anesthesiol Scand; vol. 29(4); pp. 384-388; May 1985.

Hayashibara, "AA2G"; Sep. 23, 2007, http://web.archive.org/web/20079230072010/http://www.hayashibara-intl.com/cosmetics/aa2g.html.

Helliwell, "Use of an Objective Measure of Articular Stiffness to Record Changes in Finger Joints After Intra-Articular Injection of Corticosteroid", An Theum Dis; vol. 56; pp. 71-73; 1997.

Hertzberger-Ten Cate et al., "Intra-Articular Steroids in Pauciarticular Juvenile Chronic Arthritis", Type I, Eur J Pediatr; vol. 150; pp. 170-172; 1991.

Hetherington, "Potential for Patient Harm From Intrathecal Administration of Preserved Solutions", Abstract only Med J; vol. 173(3); p. 141; Aug. 2000.

Hurst, "Adhesive Arachnoiditis and Vascular Blockage Caused by Detergents and Other Chemical Irritants: an Experimental Study", J Path Bact, vol. LXX, No. 70; pp. 167-177; 1955.

Intramed Mannitol 20% m/v Infusion, package insert, pp. 1-2 (2010) http://home.intekom.com/pharm/intramed/manitl20.html.

Jones et al., "Intra-Articular Hyaluronic Acid Compared to Intra-Articular Triamcinolone Hexacetonide in Inflammatory Knee Osteóarthritis", Osteoarthritis Cartilage, vol. 3; pp. 269-273; 1995.

Kablik et al. "Comparative physical properties of hyaluronic acid dermal fillers." Dermatol. Surg.; vol. 35(Suppl. 1); pp. 302-312; 2009.

Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.

Kulicke et al., "Visco-Elastic Properties of Sodium Hyaluronate Solutions," American Institue of Physics; 3 pages; 2008.

Laeschke, "Biocompatibility of Microparticles into Soft Tissue Fillers", Semin. Cutan. Med. Surg., vol. 23; pp. 214-217; 2004.

Lamar et al., "Antifibrosis Effect of Novel Gels in Anterior Ciliary Slerotomy (ACS)," ARVO 2002 abstract only.

Levy et al., "Lidocaine hypersensitivity after subconjunctival injection", Can J Ophthalmol 2006; vol. 41, No. 2; pp. 204-206.

Lupo; "Hyaluronic acid fillers in facial rejuvenation." Semin. Cutan. Med. Surg.; vol. 25; pp. 122-126; 2006.

Mackley et al., "Delayed-Type Hypersensitivity to Lidocaine", Arch Dermatol, vol. 139; pp. 343-346; Mar. 2003.

Mancinelli et al., "Intramuscular High-Dose Triamcinolone Acetonide in the Treatment of Severe Chronic Asthma", West J. Med; vol. 167(5); pp. 322-329; Nov. 1997.

Matsumoto et al., "Reducing the Discomfort of Lidocaine Administration through pH Buffering," Journal of Vascular and Interventional Radiology; vol. 5, No. 1; pp. 171-175; Nov. 1997.

McCarty et al., "Inflammatory Reaction After Intrasynovial Injection of Microcrystalline Adrenocorticosteroid Esters", Arthritis and Rheuymatism; vol. 7(4); pp. 359-367; 1964.

McCleland et al.; "Evlaution of Artecoll Polymethacrylate Implant for Soft-Tissue Augmentation: Biocompatibility and Chemical Chartacterization"; Plastic Reconstructive Surgery; vol. 100(6); pp. 1466-1474; Nov. 1997.

Orvisky et al., "High-molecular-weight hyaluronan—a valuable tool in testing the antioxidative activity of amphiphilic drugs stobadine and vinpocetine"; J. Pharm. Biomed. Anal.; vol. 16; pp. 419-424; 1997.

Osmitrol (generic name Mannitol),Official FDA Information, side effects and uses, pp. 1-10 (2010) http://www.drugs.com/pro/osmitrol.html.

Prestwich; "Evaluating drug efficacy and toxicology in three dimensions: using synthetic extracellular matrices in drug discovery"; Accounts of Chemical Research; vol. 41, No. 1; pp. 139-148; Jan. 2008.

Rehakova et al.; "Properties of collagen and hyaluronic acid composite materials and their modifications by chemical crosslinking," Journal of Biomedical Materials Research; vol. 30; pp. 369-372; 1996.

Remington's Pharmaceutical Science Mac Publishing Company, Easton, PA 16th Edition 1980; 1-page.

Sannino et al., "Crosslinking of Cellulose Derivatives and Hyaluronic Acid with Water-Soluble Carbodiimide," Polymer; vol. 46; pp. 11206-11212 ; 2005.

SCULPTRA® Aesthetic (injectable poly-L-lactic acid) Directions for Use, Dermik Laboratories product insert (Jul. 2009), sanofi-aventis U.S. LLC; 10 pages.

Segura et al. "Crosslinked hyaluronic acid hydrogels: a strategy to functionalize and pattern." Biomaterials; vol. 26; pp. 359-371; 2005.

Selvi et al, "Arthritis Induced by Corticosteroid Crystals", J. Rheumatology; vol. 34:3; 1 page; 2004.

Serban et al., "Modular Extracellular Matrices: Solutions for the Puzzle"; Methods; vol. 45(1)pp. 93-98; 2008.

Shu et al., "Synthesis and evaluation of injectable, in situ crosslinkable synthetic extracellular matrices for tissue engineering"; J. Biomed. Mater. Res. A.; vol. 79(4); pp. 902-912; 2006.

Silver et al., "Physical Properties of Hyaluronic Acid and Hydroxypropylmethylcellulose in Solution: Evaluation of Coating Ability"; Journal of Applied Biomaterials; vol. 5; pp. 89-98; 1994.

Smith et al., "Five Percent Lidocaine Cream Applied Simultaneously to Skin and Mucosa of the Lips Creates Excellent Anesthesia for Filler Injections", Dermatol Surg; vol. 31; pp. 1635-1637; 2005.

Tezel et al.,, "The science of hyaluronic acid dermal fillers", J. Cosmet. Laser Ther.; vol. 10; pp. 35-42; 2008.

TRB Chemedica Ophthalmic Line, VISIOL, product info., pp. 1-2; No date.

VISIOL, Viscoelstic gel for use in ocular surgery, (2010) p. 1, htt://www.trbchemedica.com/index.php/option=com_content&tas.

Waraszkiewicz et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, pp. 1215-1218, Nov. 1981.

Xia et al., "Comparison of Effects of Lidocaine Hydrochloride, Buffered Lidocaine, Diphenhydramine, and Normal Saline After Intradermal Injection", Journal of Clinical Anesthesia 14:339-343, 2002.

Yeom et al., "Effect of Cross-Linking Reagents for Hyaluronic Acid Hydrogel Dermal Fillers on Tissue Augmentation and Regeneration", Bioconjugate Chem., vol. 21; pp. 240-247; 2010.

Yui, et al., "Inflammation responsive degradation of crosslinked hyaluronic acid gels," Journal of Controlled Release, vol. 22; pp. 105-116; 1992.

Yui et al., "Photo-responsive degradation of heterogeneous hydrogels comprising crosslinked hyaluronic acid and lipid microspheres for temporal drug delivery," Journal of Controlled Release; vol. 26; pp. 141-145; 1993.

Yun et al., "Hyaluronan Microspheres for Sustained Gene Delivery and Site-Specific Targeting", Biomaterials, vol. 25, pp. 147-157, 2004.

Zheng Shu et al., "In situ crosslinkable hyaluronan hydrogels for tissue engineering." Biomaterials; vol. 25; pp. 1339-1348; 2004.

Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Lindvall et al.; "Influence of Various Compounds on the Degradation of Hyaluronic Acid by a Myeloperoxidase System"; Chemcio-Biological Interactions; vol. 90; pp. 1-12; 1994.

Weidmann; "New Hyaluronic Acid Filler for Subdermal and Long-Lasting Volume Restoration of the Face"; European Dermatology; pp. 65-68; 2009.

Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

\* cited by examiner

TUNABLY CROSSLINKED POLYSACCHARIDE COMPOSITIONS

RELATED APPLICATION

This application claims priority to U.S. Provisional Patent Application No. 60/952,770 filed on Jul. 30, 2007, which is incorporated herein by reference.

BACKGROUND OF THE INVENTION a. Field of the Invention

The present invention relates to novel biocompatible polysaccharide gel compositions, methods of their manufacture and use, and the novel crosslinkers used to make them. More specifically, the present invention relates to novel compositions of hyaluronic acid gels that are crosslinked with a novel multifunctional crosslinker, and to methods of making such crosslinked hyaluronic acid gels.

b. Background Art

Hyaluronic acid is a non-sulfated glycosaminoglycan that is distributed widely throughout the human body in connective, epithelial, and neural tissues. Hyaluronic acid is also a major component of skin, where it is involved in tissue repair. As skin ages and is repeatedly exposed to the sun's ultra violet rays, dermal cells decrease their production of hyaluronic acid and increase the rate of its degradation. Likewise, aging skin loses collagen, another natural substance necessary to keep skin youthful and resilient. Over time, the loss of hyaluronic acid and collagen causes aging skin to develop lines, wrinkles, and folds.

In the past several years, compositions of hyaluronic acid have been used in cosmetic applications to fill wrinkles, lines, folds, scars, and to enhance dermal tissue, for example, to plump lips. Because hyaluronic acid is natural to the human body, it is a generally well tolerated and fairly low risk skin augmentation product.

Originally, hyaluronic acid compositions contained particles, or microspheres, of hyaluronic acid suspended in a gel. These compositions, which are still in commercial use, tend to degrade within a few months after injection and thus require fairly frequent reinjection to maintain their skin augmenting effect. Specifically, hyaluronic acid is highly soluble in its natural state and has a rapid turnover through enzymatic and free radical metabolization.

More recently, compositions of cross-linked hyaluronic acid have been used for dermal augmentation. These hyaluronic acid compositions are typically crosslinked with a bifunctional crosslinking agent, such as butanediol diglycidyl ether (BDDE), typically with a double ether bond connecting the HA molecules to form a less water soluble polymer hydrogel network that is more resistant to degradation, and thus requires less frequent reinjection, than the non-crosslinked hyaluronic acid compositions. Some such cross-linked compositions contain fairly large particles, around approximately 50-1000 μm each, of hyaluronic acid suspended in a gel. Others are a fairly uniform consistency gel matrix of hyaluronic acid.

While these known crosslinked hyaluronic acid compositions last longer than their noncrosslinked counterparts, their duration is typically twelve months or less, thus still requiring fairly frequent reinjection. It is thus desirable to develop a hyaluronic acid composition that is biocompatible and useful as a dermal filler, but has a longer useful lifetime upon injection. Specifically, it is desirable to develop a hyaluronic acid composition that is biocompatible and injectable, but that has a higher mechanical strength, a greater resistance to enzymatic degradation, and a higher water retention than currently available compositions.

BRIEF SUMMARY OF THE INVENTION

The present invention relates to compositions of crosslinked hyaluronic acid, methods of their manufacture, and methods of their use. More specifically, the present invention relates to a process for the preparation of crosslinked hyaluronic acid, the process comprising contacting hyaluronic acid with a polyethylene glycol (PEG) based crosslinking agent. The polyethylene glycol based crosslinker agent (or crosslinker) may be bifunctional, meaning it has a PEG backbone with two reactive groups for linking to the hyaluronic acid chains. Or, the polyethylene glycol based crosslinking agent (or crosslinker) may be "multifunctional," having a PEG backbone with more than two reactive groups for linking to hyaluronic acid chains. The process may additionally include contacting the hyaluronic acid with a non-polyethylene glycol based crosslinking agent, including but not limited to BDDE or divinyl sulfone (DVS). According to some of the processes of the present invention for making a crosslinked hyaluronic acid, the polyethylene based crosslinking agent may be tetrafunctional and the hyaluronic acid may be brought into contact with the tetrafunctional crosslinking agent and with a bifunctional crosslinking agent, such as, for example, BDDE.

The present invention also relates to a process for the preparation of crosslinked hyaluronic acid, the process comprising contacting hyaluronic acid with a multifunctional crosslinking agent. The multifunctional crosslinking agent may be tri, tetra, penta, hexa, etc. functional (having more than two functional groups for reaction). In one embodiment of the present invention, the process comprises contacting hyaluronic acid with a tetrafunctional crosslinking agent, such as a 4-Arm Star PEG epoxide which is further described herein. The process may further comprise contacting the hyaluronic acid with a bifunctional crosslinking agent as well. The hyaluronic acid may be contacted with a variety of bifunctional and multifunctional crosslinking agents, and such contact may occur sequentially in any order, or the hyaluronic acid may be reacted with the various crosslinking agents in one step.

The processes of the present invention may also comprise coating hyaluronic acid compositions with polyethylene glycol based pendants. The polyethylene glycol based coating may be applied to crosslinked or uncrosslinked hyaluronic acid. In one preferred embodiment, the crosslinked hyaluronic acid compositions made according to the present invention are further coated with polyethylene glycol based pendants.

The present invention also includes compositions for soft tissue augmentation, and in particular for dermal fillers, which are prepared according to the processes of the present invention. More specifically, the present invention includes a composition for soft tissue augmentation, and particularly for use as a dermal filler, the composition comprising hyaluronic acid that has been crosslinked with at least one type of polyethylene glycol crosslinking agent. The polyethylene glycol based crosslinking agent(s) may be bifunctional, multifunctional, or a combination thereof. In one embodiment, a hyaluronic acid composition of the present invention has been crosslinked with a 4-Arm Star PEG epoxide. The compositions of the present invention may also comprise crosslinked hyaluronic acid compositions that have been prepared using more than one type of PEG crosslinking agent. For example, the compositions of the present invention may be prepared using a combination of polyethylene glycol based crosslinkers with varying numbers of functional groups and/or with varying lengths of ethylene glycol in their polymer chains or arms. The compositions of the present invention may further comprise a polyethylene glycol based coating.

The present invention further relates to dermal filler compositions comprising hyaluronic acid that has been crosslinked using at least one multifunctional crosslinking agent. The multifunctional crosslinking agent may be a multifunctional polyethylene glycol based crosslinking agent, such as a tetrafunctional polyethylene glycol based crosslinking agent, including, but not limited to, a 4-Arm Star PEG epoxide. The dermal fillers of the present invention may also comprise hyaluronic acid that has been crosslinked with a multifunctional crosslinking agent, such as a tetrafunctional polyethylene glycol, and also with a bifunctional crosslinking agent, such as BDDE, DVS, or a bifunctional polyethylene glycol.

In yet another aspect, the present invention relates to methods for repair or augmentation of the soft tissue of a patient comprising the steps of selecting the soft tissue to be repaired or augmented and injecting a composition comprising a crosslinked hylauronic acid of the present invention, as described herein, into the selected soft tissue.

The foregoing and other aspects, features, details, utilities, and advantages of the present invention will be apparent from reading the following description and claims, and from reviewing the accompanying drawings.

DETAILED DESCRIPTION OF THE INVENTION

The present invention generally relates to hyaluronic acid compositions that are crosslinked using a multifunctional crosslinking agent, methods of using such compositions, and to the novel crosslinking agents used to make such hyaluronic acid compositions. Such crosslinked hyaluronic acid compositions are useful for soft tissue augmentation, and particularly as dermal filler agents.

Figures 1, 2:
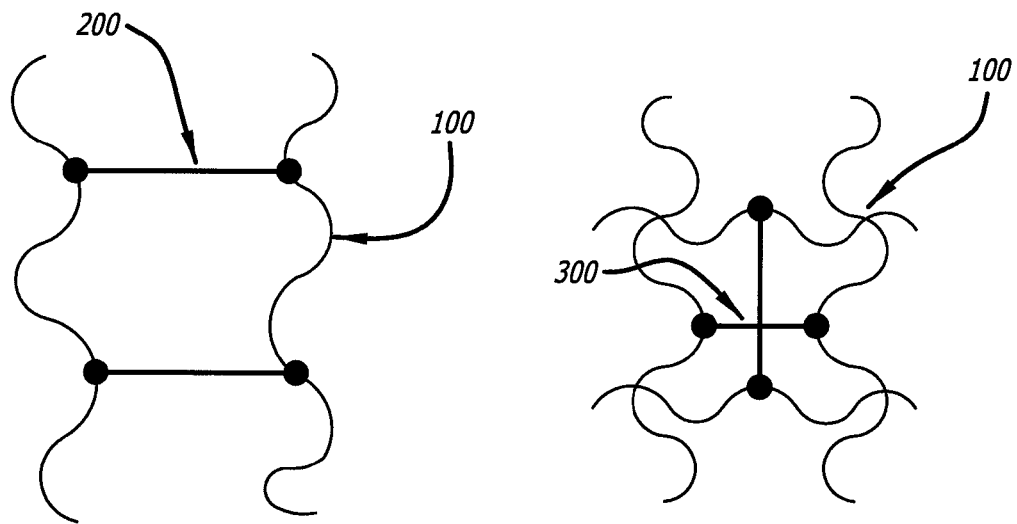
FIG. 1 depicts crosslinking of two hyaluronic acid chains with a bifunctional crosslinking agent.
FIG. 2 depicts crosslinking of four hyaluronic acid chains with a multifunctional crosslinking agent.

One aspect of this invention relates to novel catalysts for the crosslinking of hyaluronic acid. In one embodiment, the crosslinkers of the present invention are polyethylene glycol (PEG) based crosslinkers. PEG is a biocompatible polymer which is hydrophilic and inert. Because it is a polymer itself, its size (length) can be altered. Thus, the size of the PEG based crosslinker can be tuned based on the desired properties of the crosslinked hyaluronic acid. As shown in FIG. 1, in one embodiment of the present invention, the PEG based crosslinker 200 is bifunctional—both ends of the polymer chain are reactive (typically having epoxide ends) and thus capable of binding to strands of hyaluronic acid 100. In another embodiment of the present invention, the PEG based crosslinker comprises PEG of a plurality of chain lengths. The PEG based crosslinker can be made according to any PEG synthesis methods known to one of ordinary skill in the art.

The PEG based crosslinkers of the present invention may be used on their own or in combination with any another crosslinking agent suitable for making crosslinked hyaluronic acid. In one embodiment of the present invention, a combination of PEG based crosslinkers of the present invention and BDDE is used to make a crosslinked hyaluronic acid composition.

In another embodiment, the crosslinker of the present invention is a multifunctional crosslinker. As used herein, multifunctional means having more than two reactive sites on the crosslinking agent. As shown in FIG. 2, the multifunctional crosslinker 300 is able to bind more chains of hyaluronic acid 100 to one another than a bifunctional crosslinker. Thus, the multifunctional crosslinker results in hyaluronic acid compositions with greater mechanical strength (G'). The multifunctional crosslinkers of the present invention also improve the degradation of the resulting hyaluronic acid composition. Moreover, the multifunctional crosslinkers of the present invention increase the probability of each crosslinking molecule reacting with at least one hyaluronic acid strand, thereby facilitating purification and removal of unreacted crosslinking agents from the final hyaluronic acid composition.

In one embodiment of the present invention, the multifunctional crosslinker is trifunctional (contains 3 active sites). In another embodiment, the multifunctional crosslinker is tetrafunctional. In yet another embodiment, the multifunctional crosslinker is pentafunctional. In still another embodiment, the multifunctional crosslinker is hexafunctional or more. Indeed, the number of functional sites on the crosslinker of the present invention is limited only by the ability of the hyaluronic acid chains to bind to the resulting active sites on the crosslinker due to, e.g., geometry and steric hindrance. In another embodiment of the present invention, a crosslinker composition comprises multifunctional crosslinkers of at least two different functionalities (e.g. a combination of tetrafunctional crosslinkers with hexafunctional crosslinkers). In still a further embodiment, a multifunctional crosslinker is combined with a bifunctional crosslinker in varying ratios to create hyaluronic acid compositions with varying mechanical strength. Table 1 shows a few sample bifunctional to multifunctional crosslinker ratios and the mechanical strengths of the resulting hyaluronic acid gels.

Figure 3:
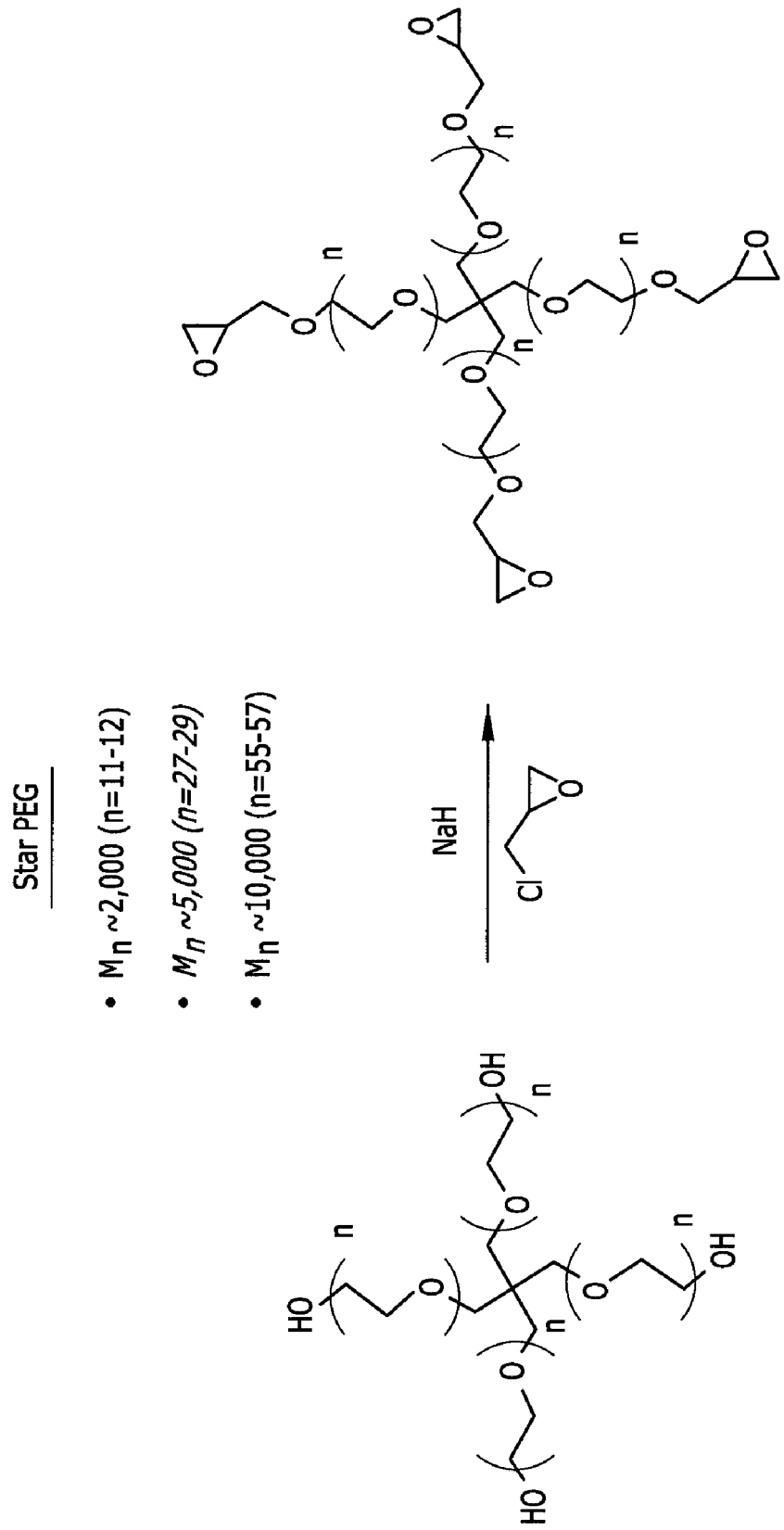
FIG. 3 depicts two chemical formulas for the tetrafunctional polyethylene glycol based crosslinking agent and its precursor of the present invention.

In a further aspect, the multifunctional crosslinker of the present invention may be a multifunctional PEG based crosslinker. A tetrafunctional PEG based crosslinker of the present invention is shown in FIG. 3. As shown in FIG. 3, in one embodiment, the present invention relates to a tetrafunctional PEG crosslinker precursor. As further shown in FIG. 3, the tetrafunctional PEG crosslinker precursor may further be reacted with an epoxide to create a novel 4-Arm Star PEG epoxide crosslinker. The epoxide tetrafunctional PEG crosslinker shown in FIG. 3 may be made from a base poly-alcohol molecule (i.e. pentaerythritol) by attaching epoxide groups and reacting with hydroxyl-PEG chains of the desired length and branching. Epoxide groups can be attached to the base poly-alcohol molecule by deprotonating the hydroxyl groups and reacting with epichlorohydrin. The epoxide rings can subsequently react with the hydroxyl groups of the PEG chains under basic conditions. In the final step of the crosslinker preparation, epoxide groups can be attached to each end of the PEG chains, thus enabling the reaction of the crosslinker with the polysaccharide molecule.

As with the bifunctional PEG based crosslinkers, described above, tetrafunctional PEG based crosslinkers (including the 4-Arm Star PEG epoxide) are of tunable size. As shown in FIG. 3, the crosslinkers may have a variety of polymer lengths in their arms, thereby affecting their mechanical properties. Moreover, by mixing the tetrafunctional based PEG crosslinkers of the present invention with a bifunctional crosslinker, such as, for example, the bifunctional PEG crosslinkers of the present invention, BDDE, DVS, and/or 1,2,7,8-diepoxyoctane, in varying ratios, the mechanical strength and hardness of the final hyaluronic acid composition may be tuned as desired.

The present invention also relates to crosslinked hyaluronic acid compositions that are made using the crosslinking agents of the present invention. In one embodiment, the hyaluronic acid compositions of the present invention comprise a PEG based crosslinker. In a further embodiment, the hyaluronic acid compositions of the present invention comprise a multifunctional PEG based crosslinker. In yet a further embodiment, the hyaluronic acid compositions comprise a tetrafunctional PEG based crosslinker. And in still a further embodiment, the hyaluronic acid compositions comprise a 4-Arm Star PEG epoxide cross linker. In other embodiments, the hyaluronic acid compositions comprise multifunctional crosslinkers as well as bifunctional crosslinkers. The hyaluronic acid compositions of the present invention may be fairly uniform gels or they may be ground into particles which can be further suspended in a gel. In one embodiment of the present invention, the hyaluronic acid composition comprises hyaluronic acid that is made with a multifunctional crosslinking agent and then ground into particles, and a gel of hyaluronic acid made with a multifunctional and/or bifunctional crosslinking agent in which the particles are suspended.

In yet another aspect of the present invention, hyaluronic acid compositions are further coated in PEG based pendant. As a biocompatible, inert, and hydrophilic polymer, PEG offers good degradation resistance to hyaluronic acid. Crosslinked or noncrosslinked hyaluronic acid particles can be coated with PEG based pendants to enhance their in vivo longevity. In one embodiment, the crosslinked hyaluronic acid compositions of the present invention are ground into particles and the particles are coated with PEG based pendants. The particles may typically be about 100 μm to 1000 μm and the coating may typically range from 2 nm to 50 nm in thickness.

The present invention also relates to methods of making hyaluronic acid compositions that are crosslinked with a PEG based crosslinker. In one embodiment, hyaluronic acid is brought into contact with a bifunctional PEG based crosslinker and allowed to react. In a further embodiment, hyaluronic acid is brought into contact with a quantity of a bifunctional crosslinker, and is then brought into contact with a quantity of a multifunctional crosslinker. The hyaluronic acid may be reacted with more than one crosslinker in either a step-wise fashion, with a lower functionality crosslinker being brought into contact first or with a higher functionality crosslinker being brought into contact first. Or, the hyaluronic acid may be reacted with a plurality of crosslinkers in one step.

Another aspect of the present invention is methods of using the novel hyaluronic acid compositions of the present invention to augment soft tissue. In one embodiment, the novel hyaluronic acid compositions of the present invention are used as dermal fillers to fill undesired lines, wrinkles, and/or folds in a patient's skin.

The following examples provide further detail regarding some of the embodiments of the present invention.

EXAMPLE 1

A multifunctional crosslinker of the present invention may be prepared from a base polyalcohol. For example, 136 mg of pentaerythritol (i.e. for the tetrafunctional PEG crosslinker) may be reacted with 100 mg of sodium hydride and subsequently with 370 mg of epichlorohydrin to attach the epoxide groups. 5000 mg of hydroxyl PEG chains (i.e. MW=1.25k) may be reacted with the epoxide terminated poly-alcohol under basic conditions (i.e. in a NaOH solution) to yield a tetrafunctional PEG hydroxyl terminated crosslinker precursor. The precursor can be reacted with an equimolar amount of epichlorohydrin as described above to produce the tetrafunctional crosslinker.

EXAMPLE 2

One embodiment of a hyaluronic acid gel according to the present invention may be prepared as follows.

One gram of sodium hyaluronate fibers (NaHA, Mw=0.5-3 MDa) is mixed with 5-10 grams of 0.01-1% sodium hudroxide solution and the mixture is left to hydrate for 1 to 5 hours. Then 20-200 mg of 1,4 butanediol diglycidyl ether (BDDE) and 0.05-2 g of 4-Arm star PEG epoxide (Mw=200-10,000 Da) are added to the NaHA gel. The mixture is mechanically homogenized, then placed in a 40-70° C. oven for 1 to 10 hours. The resulting crosslinked hydrogel is neutralized with an equimolar amount of hydrochloric acid and swelled in a phosphate buffer (PBS, pH=7.4). This hydrogel may then be mechanically homogenized.

EXAMPLE 3

To compare the characteristics of a crosslinked hyaluronic acid of the present invention to a prior art type of crosslinked hyaluronic acid, the method disclosed in Example 2 was used to prepare a batch of the novel tunably crosslinked hyaluronic acid. A similar method was used to prepare a batch of a known crosslinked hyaluronic acid, using BDDE as the only crosslinking agent (not adding any of the novel 4-Arm Star PEG epoxide) such that the molar ratio of HA to crosslinker was the same as in Example 2.

Samples from the two batches were then compared using strain sweep tests to determine gel hardness as an indicator of the degree of crosslinking of each sample. The strain sweep tests were performed on an ARES rheometer using a 50 mm parallel plate set-up. Approximately 2 to 3 ml of each sample was placed at the center of the lower plate and the gap was set to 1 mm. The test was performed at 5 Hz frequency for a range of 1-250% strain. At low values of strain, the plateau in the elastic or storage modulus G' quantifies the gel hardness.

Figure 4:
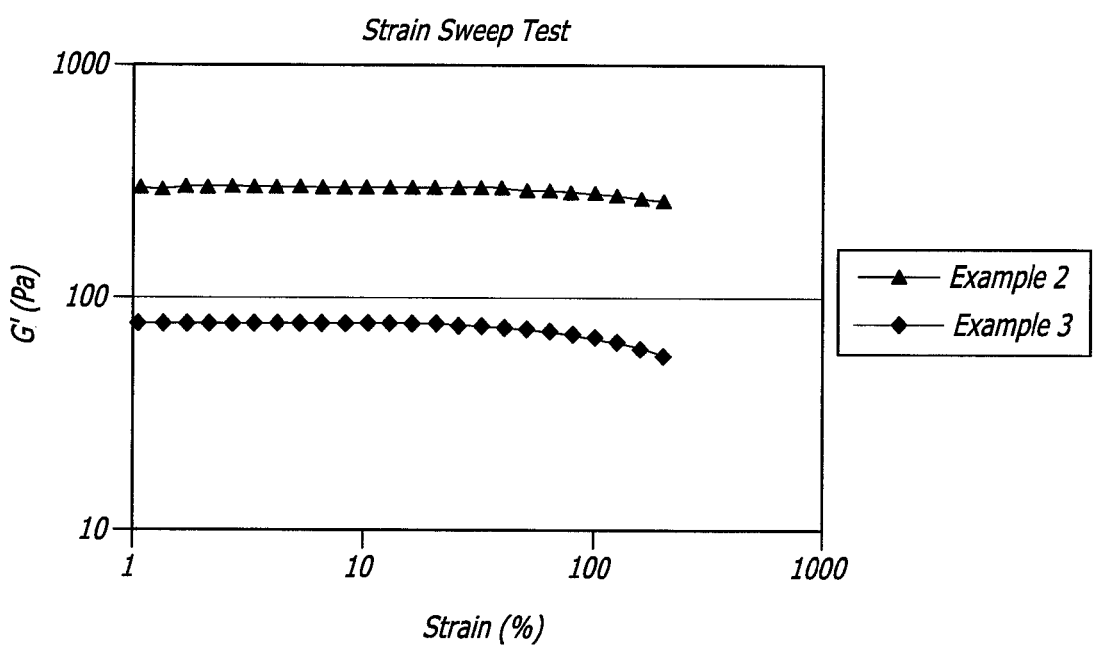
FIG. 4 is a graph showing the difference in mechanical strength between a sample a hyaluronic acid composition that was crosslinked with BDDE, and a hyaluronic acid composition that was crosslinked with a combination of BDDE and a 4-Arm Star PEG epoxide crosslinking agent of the present invention.

FIG. 4 demonstrates graphically the results of measurements made on the filling gels prepared according to the invention in comparison to prior art hydrogels. As shown in FIG. 4, the G' plateau for the hydrogel of the present invention is significantly higher than that of the prior art gel. The hydrogel of the present invention is harder and is more highly cross-linked than the prior art gel.

EXAMPLE 4

Six samples of crosslinked hyaluronic acid were prepared using bifunctional PEG and 4-Arm Star PEG epoxide crosslinkers. In each sample, the ratio of bifunctional PEG to 4-Arm Star PEG epoxide was varied, such that the molar ratio of HA to total crosslinker remained the same for all six samples. The mechanical strength of each sample was tested using the same method described above. The plateau in G' at low strain values is reported in the Table 1 below. As shown in Table 1, the plateau G' value at low strain increases as bifunctional crosslinker is replaced by equimolar amounts of the tetrafunctional crosslinker, indicating an increased degree of crosslinking.

TABLE 1

| % Bifunctional PEG | % 4-Arm Star PEG Epoxide | G' (Pa) |
| --- | --- | --- |
| 100 | 0 | 180 |
| 90 | 10 | 190 |
| 85 | 15 | 205 |
| 75 | 25 | 252 |
| 50 | 50 | 360 |
| 25 | 75 | 400 |

EXAMPLE 5

PEG based pendant coated hydrogel particles may be prepared by mixing 380 mg of hydrogel particles, such as Captique®, with 0-100 mg of epoxide terminated monofunctional PEG 2000 Da and 0.5 ml of sodium hydroxide (0.01-1% wt) and left to react for 1-10 hrs at 40-70° C. The resulting PEG based pendant coated particles may be neutralized with an equimolar amount of hydrochloric acid.

Coated particles may be compared to non-coated particles using an enzymatic degradation assay. A 0.1-10 mg quantity of hyaluronidase may be added to the hyaluronic acid particles for 10-250 mins at 37° C. followed by 0.1 ml of a 0.8 M potassium tetraborate solution and heating at 100° C. for 10 mins. The samples may be supplemented with 3 ml of a 10% wt p-dimethylaminobenzaldehyde solution in acetic acid and incubated at 37° C. for 10-120 mins. The absorbance at 585 nm may be used to quantify the hyaluronic acid degradation in each sample. The optical density (OD) values are reported in Table 2. As more PEG based pendant is used to coat the hyaluronic acid particles, the system becomes less susceptible to enzymatic degradation.

TABLE 2

| Sample (PEG:HA ratio) | Optical Density (OD) at 585 nm |
| --- | --- |
| A (0:1) | 0.750 |
| B (2:1) | 0.400 |
| C (10:1) | 0.260 |

Although only a few embodiments of this invention have been described above with a certain degree of particularity, those skilled in the art could make numerous alterations to the disclosed embodiments without departing from the spirit or scope of this invention. It is intended that all matter contained in the above description or shown in the accompanying drawings shall be interpreted as illustrative only and not limiting. Changes in detail may be made without departing from the spirit of the invention as defined in the appended claims.

What is claimed is:

1. A process for preparing a degradation resistant crosslinked hyaluronic acid hydrogel, said process comprising:
    a) hydrating sodium hyaluronate fibers in a sodium hydroxide solution to produce hydrated sodium hyaluronate fibers;
    b) mixing the sodium hyaluronate fibers with a tetrafunctional polyethylene glycol-based-epoxide crosslinking agent to create a sodium hyaluronate fiber mixture;
    c) heating the sodium hyaluronate fiber mixture at a temperature between 40° C. to 70° C. for a time period of between 1 to 10 hours to produce a crosslinked hyaluronic acid hydrogel; and
    d) reacting the crosslinked hyaluronic acid hydrogel with a monofunctional polyethylene glycol-based pendant to provide a coating;
        wherein the polyethylene glycol-based pendant coating provides degradation resistance to the crosslinked hyaluronic acid hydrogel, thereby enhancing in vivo longevity the crosslinked hyaluronic acid hydrogel, and
        wherein the process uses the tetrafunctional polyethylene glycol-based epoxide crosslinking agent as the only crosslinking agent for preparing the degradation resistant crosslinked hyaluronic acid hydrogel.

2. The process of claim 1, wherein the tetrafunctional polyethylene glycol based epoxide crosslinking agent has a molecular weight of about 200 Da to about 10,000 Da.

3. A composition for soft tissue augmentation, said composition comprising a crosslinked hyaluronic acid hydrogel obtained by the process according to claim 1 and ground into particles.

4. A process for preparing a degradation resistant crosslinked hyaluronic acid hydrogel, said process comprising:
    a) hydrating sodium hyaluronate fibers in a sodium hydroxide solution to produce hydrated sodium hyaluronate fibers;
    b) mixing the sodium hyaluronate fibers with a multifunctional polyethylene glycol-based epoxide crosslinking agent to create a sodium hyaluronate fiber mixture wherein the multifunctional polyethylene glycol-based epoxide crosslinking agent has more than two functional groups;
    c) heating the sodium hyaluronate fiber mixture at a temperature between 40° C. to 70° C. for a time period of between 1 to 10 hours to produce a crosslinked hyaluronic acid hydrogel; and
    d) reacting the crosslinked hyaluronic acid hydrogel with a monofunctional polyethylene glycol-based pendant to provide a coating;
        wherein the polyethylene glycol-based pendant coating provides degradation resistance to the crosslinked hyaluronic acid hydrogel, thereby enhancing the in vivo longevity the crosslinked hyaluronic acid hydrogel, and
        wherein the process uses the multifunctional polyethylene glycol-based epoxide crosslinking agent as the only crosslinking agent for preparing the degradation resistant crosslinked hyaluronic acid hydrogel.

5. The process of claim 4, wherein the multifunctional polyethylene glycol-based epoxide crosslinking agent is tetrafunctional.

6. The process of claim 4, wherein the multifunctional polyethylene glycol-based epoxide crosslinking agent is 4-Arm Star PEG epoxide.

7. The process of claim 4, wherein the multifunctional polyethylene glycol-based epoxide crosslinking agent is trifunctional.

8. The process of claim 4, wherein the multifunctional polyethylene glycol-based epoxide crosslinking agent is pentafunctional.

9. The process of claim 4, wherein the multifunctional polyethylene glycol-based epoxide crosslinking agent is hexafunctional.

10. A composition for soft tissue augmentation, said composition comprising a crosslinked hyaluronic acid hydrogel obtained by the process according to claim 4 and ground into particles.

11. A composition for soft tissue augmentation, said composition comprising degradation resistant crosslinked hyaluronic acid hydrogel particles, wherein said degradation resistant crosslinked hyaluronic acid hydrogel particles are prepared by a process comprising:
 a) hydrating sodium hyaluronate fibers in a sodium hydroxide solution to produce hydrated sodium hyaluronate fibers;
 b) mixing the sodium hyaluronate fibers with a tetrafunctional polyethylene glycol-based epoxide crosslinking agent to create a sodium hyaluronate fiber mixture;
 c) heating the sodium hyaluronate fiber mixture at a temperature between 40° C. to 70° C. for a time period of between 1 to 10 hours to produce a crosslinked hyaluronic acid hydrogel;
 d) grinding the crosslinked hyaluronic acid hydrogel ground into particles; and
 e) reacting the crosslinked hyaluronic acid hydrogel particles with a monofunctional polyethylene glycol-based pendant to provide a coating;
  wherein the polyethylene glycol-based pendant coating provides degradation resistance to the crosslinked hyaluronic acid hydrogel particles, thereby enhancing in vivo longevity the crosslinked hyaluronic acid hydrogel particles, and
  wherein the process uses the tetrafunctional polyethylene glycol-based epoxide crosslinking agent as the only crosslinking agent for preparing the degradation resistant crosslinked hyaluronic acid hydrogel particles.

12. The composition of claim 11, wherein said tetrafunctional polyethylene glycol based epoxide crosslinking agent is a 4-Arm Star PEG epoxide.

13. The composition of claim 11 for use as a dermal filler.

14. A dermal filler composition comprising degradation resistant crosslinked hyaluronic acid hydrogel particles, wherein said degradation resistant crosslinked hyaluronic acid hydrogel particles are prepared by a process comprising:
 a) hydrating sodium hyaluronate fibers in a sodium hydroxide solution to produce hydrated sodium hyaluronate fibers;
 b) mixing the sodium hyaluronate fibers with a multifunctional polyethylene glycol-based epoxide crosslinking agent to create a sodium hyaluronate fiber mixture wherein the multifunctional polyethylene glycol-based epoxide crosslinking agent has more than two functional groups;
 c) heating the sodium hyaluronate fiber mixture at a temperature between 40° C. to 70° C. for a time period of between 1 to 10 hours to produce a crosslinked hyaluronic acid hydrogel;
 d) grinding the crosslinked hyaluronic acid hydrogel ground into particles; and
 e) reacting the crosslinked hyaluronic acid hydrogel particles with a monofunctional polyethylene glycol-based pendant to provide a coating;
  wherein the polyethylene glycol-based pendant coating provides degradation resistance to the crosslinked hyaluronic acid hydrogel particles, thereby enhancing in vivo longevity the degradation resistance crosslinked hyaluronic acid hydrogel particles, and
  wherein the process uses the multifunctional polyethylene glycol-based epoxide crosslinking agent as the only crosslinking agent for preparing the degradation resistant crosslinked hyaluronic acid hydrogel particles.

15. The composition of claim 14, wherein said multifunctional polyethylene glycol-based epoxide crosslinking agent is a trifunctional polyethylene glycol-based epoxide crosslinking agent.

16. The dermal filler composition of claim 14, wherein the multifunctional polyethylene glycol-based epoxide crosslinking agent is a tetrafunctional polyethylene glycol-based epoxide crosslinker.

17. The composition of claim 14, wherein said multifunctional polyethylene glycol-based epoxide crosslinking agent is a pentafunctional polyethylene glycol-based epoxide crosslinking agent.

18. The composition of claim 14, wherein the multifunctional polyethylene glycol-based epoxide crosslinking agent is a hexafunctional polyethylene glycol-based epoxide crosslinking agent.

* * * * *

UNITED STATES PATENT AND TRADEMARK OFFICE
CERTIFICATE OF CORRECTION

PATENT NO. : 8,318,695 B2
APPLICATION NO. : 12/178574
DATED : November 27, 2012
INVENTOR(S) : Dimitrios Stroumpoulis et al.

It is certified that error appears in the above-identified patent and that said Letters Patent is hereby corrected as shown below:

Title Page, Item (56)

On page 2, in column 2, under "Other Publications", line 7, delete "Stardards," and insert -- Standards, --, therefor.

On page 3, in column 1, under "Other Publications", line 6, delete ""Hyroxyethyl" and insert -- "Hydroxyethyl --, therefor.

On page 3, in column 1, under "Other Publications", line 8, delete "(JUVADERM)" and insert -- (JUVEDERM) --, therefor.

On page 3, in column 1, under "Other Publications", line 49, delete "Chrondrocytes" and insert -- Chondrocytes --, therefor.

On page 3, in column 2, under "Other Publications", line 11, delete "Gonarthosis:" and insert -- Gonarthrosis: --, therefor.

On page 3, in column 2, under "Other Publications", line 15, delete "Anesthesiol" and insert -- Anaesthesiol --, therefor.

On page 3, in column 2, under "Other Publications", line 21, delete "An Theum" and insert -- Ann Rheum --, therefor.

On page 3, in column 2, under "Other Publications", line 44, delete "Institue" and insert -- Institute --, therefor.

On page 3, in column 2, under "Other Publications", line 48, delete "Slerotomy" and insert -- Sclerotomy --, therefor.

On page 3, in column 2, under "Other Publications", line 63, delete "Rheuymatism;" and insert -- Rheumatism; --, therefor.

On page 3, in column 2, under "Other Publications", line 64, delete "Evlaution" and insert -- Evaluation --, therefor.

Signed and Sealed this
Twenty-third Day of September, 2014

Michelle K. Lee
*Deputy Director of the United States Patent and Trademark Office*

On page 3, in column 2, under "Other Publications", line 66, delete "Chartacterization";" and insert -- Characterization"; --, therefor.

On page 3, in column 2, under "Other Publications", line 66, delete "Plastric" and insert -- Plastic --, therefor.

On page 4, in column 1, under "Other Publications", line 39, delete ""Viscoelstic" and insert -- Viscoelastic --, therefor.

On page 4, in column 1, under "Other Publications", line 39, delete "htt://" and insert -- http:// --, therefor.

On page 4, in column 2, under "Other Publications", line 34, delete ""Influcence" and insert -- "Influence --, therefor.

On page 4, in column 2, under "Other Publications", line 35, delete "Chemcio-" and insert -- Chemico- --, therefor.

On page 4, in column 2, under "Other Publications", line 40, delete "etal" and insert -- et al --, therefor.

On page 4, in column 2, under "Other Publications", line 41, delete "Crosslinkedwith" and insert -- Crosslinked with --, therefor.

On page 4, in column 2, under "Other Publications", line 41, delete "Glyol" and insert -- Glycol --, therefor.

On page 4, in column 2, under "Other Publications", line 42, delete "Tetracrylates";" and insert -- Tetraacrylates"; --, therefor.

In the Specification

In column 3, line 24, delete "hylauronic" and insert -- hyaluronic --, therefor.

In column 6, lines 24-25, delete "hudroxide" and insert -- hydroxide --, therefor.